United States Patent [19]
Mizutani et al.

[11] Patent Number: 6,066,660
[45] Date of Patent: May 23, 2000

[54] EMULSIFIABLE COMPOSITION FOR THE CONTROL OF INSECTS

[75] Inventors: Takaaki Mizutani, Nishinomiya; Michihiko Ikeda, Osaka; Hiroshi Kodama, Kawachinagano; Masakazu Shibayama, Takatsuki, all of Japan

[73] Assignee: Rhone-Poulenc Agrochimie, Lyons, France

[21] Appl. No.: 09/207,571

[22] Filed: Dec. 8, 1998

Related U.S. Application Data

[63] Continuation of application No. 08/849,046, filed as application No. PCT/EP95/04684, Nov. 29, 1995, abandoned.

[30] Foreign Application Priority Data

Nov. 30, 1994 [JP] Japan .................................. 6-321645

[51] Int. Cl.⁷ .......................... A01N 43/64; A01N 43/56
[52] U.S. Cl. ...................... 514/359; 514/403; 514/404; 514/406; 514/407
[58] Field of Search ..................... 514/407, 521, 514/531, 359, 403, 404, 406

[56] References Cited

U.S. PATENT DOCUMENTS

| | | | |
|---|---|---|---|
| 4,440,756 | 4/1984 | Herve et al. | 424/174 |
| 5,232,940 | 8/1993 | Hatton et al. | 514/407 |
| 5,256,679 | 10/1993 | Minamida et al. | 514/357 |
| 5,328,693 | 7/1994 | Horstmann et al. | 424/405 |
| 5,360,806 | 11/1994 | Toki et al. | 514/318 |
| 5,434,181 | 7/1995 | Kodaka et al. | 514/471 |
| 5,439,683 | 8/1995 | Hodakowski | 424/408 |
| 5,516,787 | 5/1996 | Takada | 514/407 |
| 5,747,519 | 5/1998 | Kodama et al. | 514/407 |

FOREIGN PATENT DOCUMENTS

| | | |
|---|---|---|
| 0295117 | 12/1988 | European Pat. Off. |
| 0453915 | 10/1991 | European Pat. Off. |
| 2713891 | 6/1995 | France . |
| 1473105 | 5/1977 | United Kingdom . |
| 2077104 | 12/1981 | United Kingdom . |
| 93/06089 | 4/1993 | WIPO . |
| 94/21606 | 9/1994 | WIPO . |
| 95/22902 | 8/1995 | WIPO . |

Primary Examiner—Jose' G. Dees
Assistant Examiner—Alton Pryor
Attorney, Agent, or Firm—Burns, Doane, Swecker & Mathis, L.L.P.

[57] ABSTRACT

An emulsifiable composition for the control of insects comprising as active ingredient thereof a compound of formula (I) and a pyrethroid and further comprising a weakly polar solvent, an emulsifying agent and a water-soluble solvent, wherein formula (I) is:

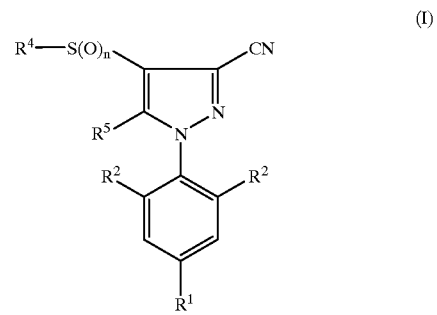

wherein:

$R^1$ is halogen, $C_1$–$C_4$ haloalkyl, $C_1$–$C_4$ haloalkoxy or $SF_5$;

$R^2$ is hydrogen or halogen, the $R^2$ substituents being identical or different;

$R^4$ is halogen, $C_1$–$C_4$ alkyl or $C_1$–$C_4$ haloalkyl;

$R^5$ is halogen, $C_1$–$C_4$ alkyl or amino; and n is 0, 1 or 2.

33 Claims, No Drawings

EMULSIFIABLE COMPOSITION FOR THE CONTROL OF INSECTS

CROSS-REFERENCE TO RELATED APPLICATIONS

This application is a continuation of application Ser. No. 08/849,046, filed Aug. 22, 1997, now abandon incorporated by reference herein in its entirety and relied upon, which is the 371 U.S. national phase of International Application No. PCT/EP95/04684, filed Nov. 29, 1995 and designating the United States.

The present invention relates to an emulsifiable composition for the control of insects and a method of use thereof. The emulsifiable compositions of the present invention derive from 1-substituted phenylpyrazole insecticides and they do not favor the formation of crystals.

The 1-substituted phenylpyrazole insecticides can be liable to generate crystallizations within the compositions during storage or use. When using such compounds for various applications, there may be problems of crystallization or recrystallization which prohibit proper and easy application. This may happen in a number of quite different practical applications such as spray applications through a nozzle which may be clogged; dilution in a tank whereby the active ingredient may thus crystallize and fall to the bottom of the tank; application to an animal's hair whereby the quality of the hair may be damaged by deposit of crystals thereon. For companion animals, a most important requirement is to have a high quality hair, which is nice and pleasant when touching or petting.

Furthermore, it is frequently the case that specialists in the control of insects, especially of termites, prepare a diluted pesticidal liquid the day before the application and utilize the remaining liquid the day after. These liquids, since they contain crystalline active ingredients, are poorly emulsified and are liable to crystallize in several hours after preparation of spraying emulsion, resulting in a great volume of liquid of no use or causing the clogging of pump nozzles employed for foam application.

In the particular situation of methods for the control of insects, especially of termites, these methods may generally be divided into two main groups. On one side is wood treatment according to which wooden parts of a house are subjected to pesticidal treatment and the other is soil treatment according to which a liquid pesticide is sprayed onto the underfloor area of a house. The application of a flowable formulation in which the active ingredient is suspended in water is becoming predominant, considering the health of the workers, for an application within the limited space under the floor. However, such dilution of water has the tendency to generate crystals. The conventional flowable formulations are not satisfactory.

Japanese Patent Publication No. 2-7282 has proposed to prevent the crystallization of some active ingredients which are not 1-substituted phenylpyrazole insecticides. Japanese Patent Application No. 50-69230 has described a liquid herbicidal composition containing as active ingredients thereof a dinitroaniline herbicide and a N-allyl-N'-alkoxy urea herbicide. It discloses also the use of an emulsifying agent and a solvent consisting of an alicyclic ketone in order to give to the composition physical stability under the conditions of transportation, storage and end use.

An object of the present invention is to provide improved emulsifiable compositions which reduce the odor of the solvent(s) and/or prevent the crystallization of the l-substituted phenylpyrazole insecticides upon dilution and/or which are generally superior to the conventional flowable formulations.

Another object of the present invention is to provide improved emulsifiable compositions which are suitable for use in combination with a foaming agent to treat the underfloor area of a house by means of a foam.

The emulsifiable compositions of the present invention contain:
- an insecticidally active compound of formula (I), and
- a pyrethroid, and
- a weakly polar solvent, and
- an emulsifying agent, and
- a water-soluble solvent, and
- optionally a foam stabilizer and/or a foaming agent, and/or a polar solvent and/or an aromatic solvent and/or other additives.

Formula (I) for the compounds used as an active ingredient in the invention is

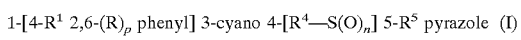

1-[4-$R^1$ 2,6-$(R)_p$ phenyl] 3-cyano 4-[$R^4$—S(O)$_n$] 5-$R^5$ pyrazole (I)

wherein:
$R^1$ is halogen, lower haloalkyl, lower haloalkoxy or $SF_5$ (lower being an integer from 1 to 4, preferably one),
$R^2$ is halogen, the various $R^2$ being identical or different,
$R^4$ is halogen, lower alkyl or haloalkyl,
$R^5$ is halogen, lower alkyl or amino,
n is 0 or 1 or 2; p is 0 or 1 or 2, preferably 2.

Halo before the name of a radical means that this radical may be substituted by one or more halogen atoms.

A preferred compound of formula (I) is the compound 5-amino-3-cyano-1-(2,6-dichloro-4-trifluoromethylphenyl)-4-trifluoromethylsulfmylpyrazole, hereinafter referred to as compound (A).

The compounds of formula (I) employed in the emulsifiable composition for the control of insects, especially of termites, of the present invention are known and described in the European Patent Publication No. 0295117 as well as in International Patent Publications WO 93/06089 and 94/21606. They are effective for the control of arthropods, plant nematodes, protozoan pests, insects, especially of termites, farm pests and the like, and arachnids such as ticks.

Examples of compounds of the pyrethroid series which may be used in the present invention include:
1. Allethrin [dl-3-allyl-2-methyl-4-oxo-2-cyclopentenyl-dl-cis, trans-chrysanthemate]
2. Ethofenprox [2-(4-ethoxyphenyl)-2-methylpropyl-3-phenoxybenzyl ether]
3. Cycloprothrin [(RS)-α-cyano-3-phenoxybenzyl (RS)-2,2dichloro-1-(4-ethoxyphenyl)cyclopropane carboxylate]
4. Cyhalothrin [(RS)-α-cyano-3-phenoxybenzyl (Z)-(1RS, 3RS) 3-(2-chloro-3,3,3-trifluoropropenyl)-2,2-dimethylcyclopropane carboxylate]
5. Cyfluthrin [(RS)-α-cyano-4-fluoro-3-phenoxybenzyl (1RS, 3RS)-(1RS, 3RS)-3-(2,2-dichlorovinyl)-2,2-dimethylcyclopropane carboxylate]
6. Cypermethrin [(RS)-α-cyano-3-phenoxybenzyl (1RS, 3RS)-(1RS, 3SR)-3-(2,2-dichlorovinyl)-2,2-dimethylcyclopropane carboxylate]
7. Pyrethrin
8. Tralomethrin [(S)-α-cyano-3-phenoxybenzyl (1R, 3S)-2,2-dimethyl-3-(1,2,2,2-tetrabromoethyl)cyclopropane carboxylate]
9. Fenvalerate [(RS)-α-cyano-3-phenoxybenzyl (RS)-2-(4-chlorophenyl)-3-methylbutanoate]
10. Fenpropathrin [(RS)-α-cyano-3-phenoxybenzyl-2,2,3,3-tetramethylcyclopropane carboxylate]
11. Flucythrinate [(RS)-α-cyano-3-phenoxybenzyl-(S)-2-(4-difluoromethoxyphenyl)-3-methylbutylate]

12. Permethrin [3-phenoxybenzyl (1RS, 3RS)-(1RS, 3RS)-(2,2-dichlorovinyl)-2,2-dimethylcyclopropane carboxylate]
13. Bifenthrin [2-methylbiphenyl-3-yl-methyl(Z)-(1RS, 3RS)-3-(2-chloro-3,3,3-trifluoroprop-1-enyl)-2,2-dimethylcyclopropane carboxylate]
14. Silafluofen [4-ethoxyphenyl-[3-(3-phenoxy4-fluorophenyl)propyl](dimethyl)-silane]
15. Resmethrin [5-benzyl-3-furylmethyl dl-cis, transchrysanthemate]
16. Tefluthrin [2,3,5,6-tetrafluoro-4-methylbenzyl-(1 RS)-cis-3-(Z-2-chloro-3,3,3-trifluoroprop-1-enyl)-2,2-dimethylcyclopropane carboxylate]
17. Acrinathrin [(S)-α-cyano-3-phenoxybenzyl (Z)-(1R, 3S)-2,2-dimethyl-3-[2-(2,2,2-trifluoro-1-trifluoromethylethoxycarbonyl)vinyl]cyclopropane carboxylate]
18. Prarethirin [(RS)-2-methyl-4-oxo-3-prop-2-enylcyclopent-2-enyl (1RS)-cis-trans-2,2-dimethyl-3-(2-methylprop-1-enyl)cyclopropane carboxylate]
19. Cismethrin [5-benzyl-3-firylmethyl (1R)-trans-2,2-dimethyl-3-(2-methylprop-1-enyl)cyclopropane carboxylate]
20. d-Phenothrin [3-phenoxybenzyl (1RS)-cis-trans-2,2-dimethyl-3-(2-methylprop-1-enyl)cyclopropane carboxylate]
21. Deltamethrin [(S)-(α-cyano-3-phenoxybenzyl (1R)-cis-3-(2,2-dibromovinyl)-2,2-dimethylcyclopropane carboxylate]
22. Tetramethrin [cyclohex-1-ene-1,2-dicarboximidomethyl-(1RS, 3RS, 1RS, 3SR)-2,2-dimethyl-3-(2-methylprop-1-enyl)cyclopropane carboxylate]
23. Fluvalinate [(RS)-α-cyano-3-phenoxybenzyl N-(2-chloro-α,α,α-trifluoro-p-tolyl)-DL-valinate].

Even though the proportions of each component of the compositions of the invention may vary within a broad range of values, the advantageous compositions which are further preferred are those which comprise, in proportions indicated as percentage by weight, which are the same as weight parts per 100 weight parts of the compositions:

0.2 to 10% of compound of formula (I), preferably 0.5 to 5% (more preferably 1 to 5%), and/or 0.1 to 10% of pyrethroid(s), and/or 1 to 15% of weakly polar solvent(s) (more particularly 1 to 10% and preferably 2 to 10%), and/or 5 to 20% of emulsifying agent(s), and/or optionally 1 to 5% of foam stabilizer(s), and/or at least one water soluble solvent as a complement up to 100%; the proportion of this (these) solvent(s) in the composition of the invention is generally more than 40%, preferably more than 60%, optionally 0 to 15% of polar solvent(s) and optionally 0 to 20% of aromatic solvent(s) and optionally other additives.

Weakly polar solvents which may be used in the invention are generally those which have a positive dipolar moment, preferably higher than 1 (the unit is the debye), and a solubility in water (at 20° C.) of less than 10%. These weakly polar solvent(s) are preferably selected among the cyclic amides and the glycolic ether solvents.

Examples of cyclic amides which may be used are N-octyl-2-pyrrolidone, N-dodecyl-2-pyrrolidone and N-dodecyl-caprolactam.

Examples of weakly polar solvent(s) of the glycolic ether type are: ethylene glycol monophenyl ether, ethylene glycol monohexyl ether, ethylene glycol mono-2-ethylhexyl ether, ethylene glycol dibutyl ether, diethylene glycol dibutyl ether, propylene glycol monophenyl ether, dipropylene glycol monopropyl ether, ethylene glycol monobenzyl ether and the like. A preferred glycol solvent is diethylene glycol mono-2-ethylhexyl ether.

Emulsifying agents which may be used are one or more of those selected from nonionic or anionic emulsifying agents. Examples of nonionic emulsifying agents which may be mentioned include polyoxyethylenealkylphenylether, polyoxyethylenealkylether, polyethyleneglycol fatty ester, sorbitan fatty ester, polyoxyethylene sorbitan fatty ester, polyoxyethylenesorbitan fatty ester, polyoxyethylenepolyoxypropylenealkylether, polyoxyethylene castor oil. Examples of anionic emulsifying agents which may be mentioned include alkyl sulfates, polyoxyethylenealkylether sulfates, sulfosuccinates, taurine derivatives, sarcosine derivatives, phosphoric esters, alkylbenzenesulfonates and the like. A three-component mixture consisting of polyoxyethylenestyrylphenylether, polyoxyethylene castor oil and calcium allylbenzenesulfonate as well as the ammonium salt of polyoxyethylenenonylphenylether sulfate are particularly preferred.

Foam stabilizers may be used as an additive for keeping the composition in a stable foaming state at the time of foam application. Examples of foam stabilizers which may be used are one or more higher alcohols, preferably a fatty alcohol, and more preferably an alcohol selected from the group consisting of decyl alcohol, dodecyl alcohol, tetradecyl alcohol, hexadecyl alcohol and the like.

Water-soluble solvents which may be used are one or more of the glycol ethers selected from those having the general formula (II):

$$RO(CH_2CH_2O)_qH \quad (II)$$

wherein R represents $C_1$–$C_6$ alkyl and q is an integer of 1 to 8. Examples of these glycol ethers include diethyleneglycol monomethyl ether, diethyleneglycol monoethyl ether, diethyleneglycol monopropyl ether, diethyleneglycol monobutyl ether, triethyleneglycol monomethyl ether, triethyleneglycol monoethyl ether, triethyleneglycol monopropyl ether, triethyleneglycol monobutyl ether, polyethyleneglycol (q=4 to 6) monomethyl ether.

Polar solvents and/or aromatic solvents may also be used as desired in the composition of the present invention. Polar solvents which are not weakly polar solvents are generally those which have a positive dipolar moment, preferably higher than 1 (the unit is the debye) while having a solubility in water higher than 10%. Such polar solvents include cyclic amides or lactones such as N-methyl-2-pyrrolidone, N-cyclohexyl-2-pyrrolidone, caprolactone, butyrolactone; and glycol ethers such as tripropyleneglycol monomethyl ether, diethyleneglycol dimethyl ether.

Suitable aromatic solvents are those which are in liquid state at normal temperature and have a boiling point of at least 200° C. They may be selected from a petroleum fraction, a catalytic cracked oil fraction or synthetic oil and the like. Examples which may be mentioned include: mono- or poly-alkylbenzenes such as alkylbenzene or trimethylbenzene; naphthalenes such as methylnaphthalene, dimethylnaphthalene, dimethylmonopropylnaphthalene, dimethyldipropylnaphthalene or phenylxylylnaphthalene; alkyldiphenylalkanes such as 1-phenyl-1-xylylethane or alkyldiphenylethane; indene derivatives; triallyldialkanes such as triallydiethane; dibenzylethers; diester phthalates and the like.

Foaming agents which may be admixed into the emulsifiable composition diluted with water at the time of application may comprise a surface active agent and a foam stabilizer as well as a solvent or water as desired. The amounts of these foaming agents may vary in a large range according to the amount of foam which is desired for the particular application. Suitable surface active agents may be, for example, sodium salts of polyoxyethylenealkylphenylether sulfate, ammonium salts of polyoxyethylenealkylphenylether sulfate, amine salts of polyoxyethylenealkylphenylether sulfate, sodium salts of alkylsulfates, amine salts of alkyl sulfates, ammonium salts of alkylsulfates and the like. Foam stabilizers and solvents may be the same chemical compounds as those which were used in the composition of the present invention. When used together with a foaming agent, the composition of the present invention can be diluted with water to give a foamy emulsion of required concentration and the obtained emulsion can be applied to the limited space under the floor by means of a pump-driven spraying nozzle.

Emulsifiable compositions of the present invention may be prepared by any of conventional procedures suitable for emulsifiable concentrates.

Emulsifiable compositions for the control of termites according to the present invention exhibit a remarkable effect against house damage from insects, especially of insects, especially of termites, including *Coptotermes formosanus* (Shiraki), *Reticulitermes speratus* (Kolbe), *Odontotermes formosanus* (Shiraki) and *Coptotermes domesticus* (Haviland). When a house is treated with foam application, insects, especially termites, can be exterminated completely and the treated wooden parts can be protected against boring by insects.

The invention relates also to insecticidal compositions as hereinbefore described which are useful to treat the house and especially the underfloor area of the house, particularly against termites, and which further comprise a foaming agent. The corresponding method of treatment using such compositions is also part of the invention.

The invention still further relates to a method for the control of insects, especially of termites, whereby an effective amount of a composition as hereinbefore described is applied to the locus (which may be a cropping area) which is infested or expected to be infested by said pests, the applied dose of the active ingredients being preferably in the range from 0.01 to 15.0 mg/m$^2$, and more preferably in the range from 0.1 to 5.0 mg/m$^2$.

The compositions of the invention are useful for the treatment of many insects, especially termites, fleas, and more generally insects or arachnids such as ticks which infest or are expected to infest dogs or cats or other companion animals, as well as other insects as cited in European Patent Publication No. 0295117, which is herein incorporated by reference.

The invention still farther relates to a method of control of fleas or ticks or insects from dogs and cats whereby an effective amount of a composition as hereinbefore described is applied to the animal which is infested or expected to be infested by said pests.

The present invention is illustrated by the following examples, comparative examples and experimental examples, but is not limited to the details thereof. Unless otherwise specified, parts are by weight.

EXAMPLE 1

1 part of the compound (A), 1 part of bifenthrin, 3 parts of N-octyl-2-pyrrolidone, 7 parts of dimethyldipropylnaphthalene, 5 parts of lauryl alcohol, 10 parts of a mixture of polyoxyethylenealkylphenylether, polyoxyethylene castor oil and calcium alkyl benzene sulfonate. ("Hymal 1071", available from Matsumoto Yushi Seiyaky Inc.), 2 parts of the ammonium salt of polyoxyethylenenonylphenylether sulfate ("Hytenol N-08", available from Daiichi Kogyo Seiyaku Inc.) and 71 parts of polyoxyethyleneglycol monomethyl ether were homogeneously dissolved to obtain an emulsifiable composition of the present invention.

EXAMPLES 2 TO 28

In each of these examples, an emusifiable composition of the present invention was prepared in a similar manner to Example 1 according to the corresponding formulation shown in the Tables 1 to 6.

TABLE 1

| EXAMPLE N° | 1 | 2 | 3 | 4 | 5 | 6 |
|---|---|---|---|---|---|---|
| Compound (A) | 1.0 | 1.0 | 5.0 | 5.0 | 1.0 | 1.0 |
| Bifenthrin | 1.0 | 1.0 | 1.0 | 5.0 | 1.0 | 1.0 |
| N-Octyl-2-pyrrolidone | 3.0 | 5.0 | 10.0 | 10.0 | 3.0 | 3.0 |
| Dimethyldipropylnaphthalene | 7.0 | 10.0 | 20.0 | 20.0 | 20.0 | 7.0 |
| Hymal 1071 | 10.0 | 10.0 | 10.0 | 10.0 | 10.0 | 10.0 |
| Hytenol N-08 | 2.0 | 2.0 | 2.0 | 2.0 | 2.0 | 2.0 |
| Dodecylalcohol | 5.0 | 5.0 | 5.0 | 5.0 | 5.0 | 1.0 |
| Polyoxyethylenemonomethylether | 71.0 | 66.0 | 47.0 | 43.0 | 58.0 | 75.0 |
| TOTAL | 100.0 | 100.0 | 100.0 | 100.0 | 100.0 | 100.0 |

TABLE 2

| EXAMPLE N° | 7 | 8 | 9 | 10 | 11 |
|---|---|---|---|---|---|
| Compound (A) | 1.0 | 1.0 | 1.0 | 1.0 | 1.0 |
| Bifenthrin | 5.0 | 1.0 | 5.0 | | |
| Fenvalerate | | | | 1.0 | |
| Cypermethrin | | | | | 1.0 |
| N-Octyl-2-pyrrolidone | 3.0 | | | 3.0 | 3.0 |
| N-dodecyl-2-pyrrolidone | | 3.0 | | | |
| N-dodecyl-caprolacam | | | 3.0 | | |
| Dimethyldipropylnaphthalene | 10.0 | 7.0 | 7.0 | 7.0 | 7.0 |
| Hymal 1071 | 10.0 | 10.0 | 10.0 | 10.0 | 10.0 |
| Hytenol N-08 | 2.0 | 2.0 | 2.0 | 2.0 | 2.0 |
| Dodecylalcohol | 5.0 | 5.0 | 5.0 | 5.0 | 5.0 |
| Polyoxyethylenemonomethylether | 64.0 | 71.0 | 67.0 | 71.0 | 71.0 |
| TOTAL | 100.0 | 100.0 | 100.0 | 100.0 | 100.0 |

TABLE 3

| EXAMPLE N° | 12 | 13 | 14 | 15 | 16 |
|---|---|---|---|---|---|
| Compound (A) | 1.0 | 1.0 | 1.0 | 1.0 | 1.0 |
| Permethrin | 1.0 | | | | |
| Tralomethrin | | 1.0 | | | |
| Fluvalinate | | | 1.0 | | |
| Cyfluthrin | | | | 1.0 | |
| Ethofenprox | | | | | 1.0 |
| N-Octyl-2-pyrrolidone | 3.0 | 3.0 | 3.0 | 3.0 | 3.0 |
| Dimethyldipropylnaphthalene | 7.0 | 7.0 | 7.0 | 7.0 | 7.0 |
| Hymal 1071 | 10.0 | 10.0 | 10.0 | 10.0 | 10.0 |
| Hytenol N-08 | 2.0 | 2.0 | 2.0 | 2.0 | 2.0 |
| Dodecylalcohol | 5.0 | 5.0 | 5.0 | 5.0 | 5.0 |
| Polyoxyethylenemonomethylether | 71.0 | 71.0 | 71.0 | 71.0 | 71.0 |
| TOTAL | 100.0 | 100.0 | 100.0 | 100.0 | 100.0 |

TABLE 4

| EXAMPLE N° | 17 | 18 | 19 | 20 | 21 |
|---|---|---|---|---|---|
| Compound (A) | 1.0 | 1.0 | 1.0 | 1.0 | 1.0 |
| Bifenthrin |  | 1.0 | 1.0 | 1.0 | 1.0 |
| Silafluorfen | 1.0 |  |  |  |  |
| N-Octyl-2-pyrrolidone | 3.0 | 2.0 | 2.0 | 2.0 | 3.0 |
| N-methyl-2-pyrrolidone |  | 0.5 |  |  |  |
| Cyclohexanone |  |  | 0.5 |  |  |
| N,N-dimethylformamide |  |  |  | 0.5 |  |
| Dimethyldipropylnaphthalene | 7.0 | 7.5 | 7.5 | 7.5 |  |
| Dimethylmonopropylnaphthalene |  |  |  |  | 7.0 |
| Hymal 1071 | 10.0 | 10.0 | 10.0 | 10.0 | 10.0 |
| Hytenol N-08 | 2.0 | 2.0 | 2.0 | 2.0 | 2.0 |
| Dodecylalcohol | 5.0 | 5.0 | 5.0 | 5.0 | 5.0 |
| Polyoxyethylenemonomethylether | 71.0 | 71.0 | 71.0 | 71.0 | 71.0 |
| TOTAL | 100.0 | 100.0 | 100.0 | 100.0 | 100.0 |

TABLE 5

| EXAMPLE N° | 22 | 23 | 24 |
|---|---|---|---|
| Compound (A) | 1.0 | 1.0 | 1.0 |
| Bifenthrin | 1.0 | 1.0 | 1.0 |
| N-Octyl-2-pyrrolidone | 3.0 | 3.0 | 2.0 |
| N-methyl-2-pyrrolidone | 0.5 |  | 0.5 |
| Dimethyldipropylnaphthalene |  | 5.0 | 5.0 |
| Dimethylmonopropylnaphthalene | 7.5 | 5.0 | 5.0 |
| Hymal 1071 | 10.0 | 10.0 | 10.0 |
| Hytenol N-08 | 2.0 | 2.0 | 2.0 |
| Dodecylalcohol | 5.0 | 5.0 | 5.0 |
| Polyoxyethylenemonomethylether | 70.0 | 68.0 | 68.5 |
| TOTAL | 100.0 | 100.0 | 100.0 |

TABLE 6

| EXAMPLE N° | 25 | 26 | 27 | 28 |
|---|---|---|---|---|
| Compound (A) | 1.0 | 1.0 | 1.0 | 1.0 |
| Bifenthrin | 1.0 | 1.0 | 1.0 | 1.0 |
| ethylene glycol mono 2-ethylhexyl ether | 20.0 |  |  | 18.0 |
| ethylene glycol mono hexyl ether |  | 20.0 |  |  |
| ethylene glycol mono benzyl ether |  |  | 20.0 |  |
| N-methyl-2-pyrrolidone |  |  |  | 2.0 |
| Hymal 1071 | 10.0 | 10.0 | 10.0 | 10.0 |
| Hytenol N-08 | 2.0 | 2.0 | 2.0 | 2.0 |
| Dodecylalcohol | 5.0 | 5.0 | 5.0 | 5.0 |
| Polyoxyethylenemonomethylether | 61.0 | 61.0 | 61.0 | 61.0 |
| TOTAL | 100.0 | 100.0 | 100.0 | 100.0 |

Comparative Examples 1 and 2

In each of these examples, an emulsifiable composition was prepared in a similar manner to Example 1 according to the corresponding formulation shown in Table 7.

TABLE 7

| COMPARATIVE EXAMPLES N° | 1 | 2 |
|---|---|---|
| Compound (A) | 1.0 | 1.0 |
| Bifenthrin | 1.0 | 1.0 |
| N-methyl-2-pyrrolidone | 3.0 |  |
| Dimethyldipropylnaphthalene | 7.0 |  |
| Hymal 1071 | 10.0 |  |
| Hytenol N-08 | 2.0 |  |
| Solpol 355X |  | 10.0 |

TABLE 7-continued

| COMPARATIVE EXAMPLES N° | 1 | 2 |
|---|---|---|
| Dodecylalcohol | 5.0 |  |
| Polyoxyethylenemonomethylether | 71.0 |  |
| Xylene |  | 88.0 |
| TOTAL | 100.0 | 100.0 |

Solpol 355X (mixture of polyoxyalkyleneallylphenylether, polyoxyallylene allylphenylether condensate and allylbenzene calcium sulfonate, available from Matsumoto Yushi Seiyaku Inc.)

Experimental Example 1

Crystallization test in emulsion

To a 100 milliliter beaker, 100 ml of 3° hard water was introduced, 1.0 g of an emulsifiable composition prepared according to each of the above examples and comparative examples was added thereto, then stirred and mixed well. After being left to stand at 5° C. for 24 hours, the obtained emulsion was passed through a sieve of 45 mm opening, then the amount of crystals remaining on the sieve was evaluated according to the following criterion by visual observation. The results are shown in Table 7.

No crystals or crystallization was observed for any of the Examples 1 to 28. On the contrary, large amounts of crystals and crystallization were observed for Comparative Example 1, and small amounts of crystals and crystallization were observed for Comparative Example 2.

Experimental Example 2

Foaming test

An emulsifiable composition prepared according to each of the Examples and Comparative Examples was diluted in water to the predetermined dilution and then 3% of an ordinary commercial foaming agent ("Dolfoam", available from Nihon Noyaku Inc.) was added thereto. The obtained mixture was made to foam by means of a foam spraying machine. The foaming property was evaluated by visual observation. No foaming was observed in Comparative Example 2. Foaming equal to that of "Dolfoam" was observed for Examples 1 and 18 and Comparative Example 1.

The emulsifiable compositions for the control of insects, especially of insects, particularly of termites, of the present invention, when diluted in water to give a spraying emulsion proper to application, were observed not to result in any crystallization and thus were found to be useful as foaming preparations for the control of insects, especially of termites.

What is claimed is:
1. An emulsifiable composition for the control of insects comprising as active ingredients thereof an insecticidally effective amount of a pyrethroid and a compound of the formula:

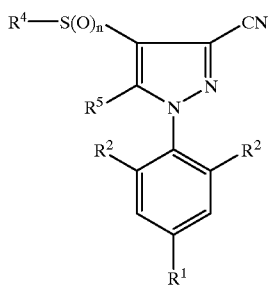

wherein
R¹ is halogen, $C_1$–$C_4$ haloalkyl, $C_1$–$C_4$ haloalkoxy or $SF_5$;
R² is hydrogen or halogen, the R² substituents being identical or different;
R⁴ is halogen, $C_1$–$C_4$ alkyl or $C_1$–$C_4$ haloalkyl;
R⁵ is halogen, $C_1$–$C_4$ alkyl or amino; and
n is 0, 1 or 2;
said composition further comprising a weakly polar solvent having a dipole moment higher than 1 and a water solubility of less than 10%, an emulsifying agent, and a water-soluble solvent which has the formula $RO(CH_2CH_2O)_qH$, wherein R is $C_1$–$C_6$ alkyl and q is an integer of 1 to 8 said composition being capable of dilution with water without formation of crystals.

2. A composition according to claim 1, wherein the compound of formula (I) is 5-amino-3-cyano-1-(2,6-dichloro-4-trifluoromethylphenyl)4-trifluoromethylsulfinylpyrazole.

3. A composition according to claim 1, wherein the pyrethroid is allethrin, ethofenprox, cycloprothrin, cyhalothrin, cyfluthrin, cypermethrin, pyrethrin, tralomethrin, fenvalerate, fenpropathrin, flucythrinate, permethrin, bifenthrin, silafluofen, resmethrin, tefluthrin, acrinathrin, prarethrin, cismethrin, d-phenothrin, deltamethrin, tetramethrin, or fluvalinate.

4. A composition according to claim 1, comprising a weakly polar solvent selected from the group consisting of N-octyl-2-pyrrolidone, N-dodecyl-2-pyrrolidone, N-dodecylcaprolactam and glycolic ethers.

5. A composition according to claim 1, comprising a nonionic or anionic emulsifying agent.

6. A composition according to claim 1, wherein the solvent of the formula $RO(CH_2CH_2O)_qH$ is diethyleneglycol monomethyl ether, diethyleneglycol monoethyl ether, diethyleneglycol monopropyl ether, diethyleneglycol monobutyl ether, triethyleneglycol monomethyl ether, triethyleneglycol monoethyl ether, triethyleneglycol monopropyl ether, triethyleneglycol monobutyl ether or polyethyleneglycol monomethyl ether.

7. A composition according to claim 1, comprising a foam stabilizer which is a higher alcohol.

8. A composition according to claim 7, wherein the higher alcohol is a fatty alcohol.

9. A composition according to claim 8, wherein the fatty alcohol is decyl alcohol, dodecyl alcohol, tetradecyl alcohol or hexadecyl alcohol.

10. A composition according to claim 1, further comprising a polar solvent which has a positive dipolar moment higher than 1 and a solubility in water higher than 10%.

11. A composition according to claim 10, wherein said polar solvent is N-methyl-2-pyrrolidone, N-cyclohexyl-2-pyrrolidone, caprolactone, butyrolactone, tripropyleneglycol monomethyl ether or diethyleneglycol dimethyl ether.

12. A composition according to claim 1, comprising an aromatic solvent which is in liquid state at a temperature below 30° C.

13. A composition according to claim 1, comprising an aromatic solvent having a boiling point of at least 200° C.

14. A composition according to claim 12, wherein the aromatic solvent has a boiling point of at least 200° C.

15. A composition according to claim 1, wherein the weight ratio of the compound of formula (I) to the pyrethroid is in the range of 1 to 10.

16. A composition according to claim 1, further comprising at least one member selected from the group consisting of a foaming agent and a foam stabilizer.

17. A composition according to claim 1, comprising:
 0.2 to 10% of compound of formula (I);
 0.1 to 10% of pyrethroid;
 1 to 15% of weakly polar solvent;
 5 to 20% of emulsifying agent;
 0 to 5% of foam stabilizer;
 0 to 15% of polar solvent;
 0 to 20% of aromatic solvent; and
 at least one water-soluble solvent as a complement up to 100%.

18. A composition according to claim 17, comprising 0.5 to 5% of compound of formula (I).

19. A composition according to claim 18, comprising 1 to 5% of compound of formula (I).

20. A composition according to claim 1, further comprising a foaming agent and being formulated for use in treating the underfloor area of a house against termites.

21. A method for controlling termites or arachnids comprising applying an insecticidally effective amount of a composition according to claim 1 to a locus which is infested or expected to be infested by termites or arachnids, the applied dose of the active ingredients being in the range from 0.01 to 15.0 mg/m².

22. A method according to claim 21, wherein the applied dose of the active ingredients is in the range from 0.1 mg to 5 mg/m².

23. A method for treating a house which is infested or expected to be infested boy termites, said method comprising applying a composition according to claim 20 to the underfloor area of the house.

24. A method for controlling insects or arachnids which infest animals, said method comprising applying an insecticidally effective amount of a composition according to claim 1 to an animal which is infested or expected to be infested by said insects or arachnids.

25. A method according to claim 24 wherein the animal is a dog or cat and the insects or arachnids are fleas or ticks.

26. A method for controlling insects according to claim 24, wherein the applied dose of the active ingredients is 0.1 to 100 mg per kilogram of body weight of the animal.

27. A method according to claim 25, wherein the applied dose of the active ingredients is 0.1 to 100 mg per kilogram of body weight of the animal.

28. A method according to claim 26, wherein the applied dose of the active ingredients is 2 to 20 mg per kilogram of body weight of the animal.

29. A method according to claim 27, wherein the applied dose of the active ingredients is 2 to 20 mg per kilogram of body weight of the animal.

30. An emulsifiable composition for the control of termites comprising as active ingredients thereof an insecticidally effective amount of 5-amino-3-cyano-1-(2,6-dichloro-4-trifluoromethylphenyl)-4-trifluoromethylsulfmylpyrazole and a pyrethroid, and further comprising a weakly polar solvent which is N-octyl-2-pyrrolidone, N-dodecyl-2-pyrrolidone or N-dodecylcaprolactam, an emulsifying agent, a foam stabilizer and a water-soluble solvent which has the formula $RO(CH_2CH_2O)_nH$, wherein R is $C_1$–$C_6$ alkyl and n is an integer of 1 to 8 composition being capable of dilution with water without formation of crystals.

31. A composition according to claim 30, comprising 1 to 5 parts by weight of 5-amino-3-cyano-1-(2,6-dichloro-4-trifluoromethylphenyl)-4-trifluoromethylsulfinylpyrazole, 0.1 to 10 parts by weight of pyrethroid, 1 to 10 parts by weight of weakly polar solvent, 5 to 20 parts by weight of emulsifying agent and 1 to 5 parts by weight of foam stabilizer.

32. A composition according to claim wherein the pyrethroid is allethrin, ethofenprox, cycloprothrin, cyhalothrin, cyfluthrin, cypermethrin, pyrethrin, tralomethrin, fenvalerate, fenpropathrin, flucynthrinate, permethrin, bifenthrin, silafluorfen, resmethrin, tefluthrin, acrinathrin, prarethrin, cismethrin, d-phenothrin, deltamethrin, tetramethrin or fluvalinate.

33. A composition according to claim 30, said composition further comprising water and a foaming agent for use in treating the underfloor area of a house against termites.

* * * * *

UNITED STATES PATENT AND TRADEMARK OFFICE
CERTIFICATE OF CORRECTION

PATENT NO.    : 6,066,660
DATED         : March 23, 2000
INVENTOR(S)   : Mizutoni et al.

It is certified that error appears in the above-identified patent and that said Letters Patent is hereby corrected as shown below:

<u>Title page,</u>
Item [56], FOREIGN PATENT DOCUMENTS, add -- WO 96/01047 --

Signed and Sealed this

Sixth Day of May, 2003

JAMES E. ROGAN
*Director of the United States Patent and Trademark Office*